United States Patent
Macaluso et al.

(10) Patent No.: US 10,695,316 B2
(45) Date of Patent: Jun. 30, 2020

(54) METHODS OF HEATING CANNABIS PLANT MATERIAL

(71) Applicants: Virgil Macaluso, Independence, KS (US); William G. Bale, Edina, MN (US); Catalytic Industrial Group, Inc., Independence, KS (US)

(72) Inventors: Virgil Macaluso, Independence, KS (US); Corey Lowdon, Independence, KS (US); Shih-Shin Chou, Independence, KS (US)

(73) Assignees: Virgil Macaluso, Independence, KS (US); William G. Bale, Edina, MN (US); Catalytic Industrial Group, Inc., Independence, KS (US)

( * ) Notice: Subject to any disclaimer, the term of this patent is extended or adjusted under 35 U.S.C. 154(b) by 0 days.

(21) Appl. No.: 16/459,771

(22) Filed: Jul. 2, 2019

(65) Prior Publication Data
US 2020/0009109 A1    Jan. 9, 2020

Related U.S. Application Data

(60) Provisional application No. 62/693,651, filed on Jul. 3, 2018.

(51) Int. Cl.
*A61K 31/352* (2006.01)
*A61K 36/185* (2006.01)
*A61K 31/05* (2006.01)
*A61K 45/06* (2006.01)
*A01G 7/00* (2006.01)
*C07C 37/68* (2006.01)

(52) U.S. Cl.
CPC .......... *A61K 31/352* (2013.01); *A61K 36/185* (2013.01); *A01G 7/00* (2013.01); *A61K 31/05* (2013.01); *A61K 45/06* (2013.01); *A61K 2236/37* (2013.01); *C07C 37/68* (2013.01)

(58) Field of Classification Search
None
See application file for complete search history.

(56) References Cited

U.S. PATENT DOCUMENTS

| | | | |
|---|---|---|---|
| 4,984,587 A | 1/1991 | Neville | |
| 5,557,858 A | 9/1996 | Macaluso et al. | |
| 5,956,865 A | 9/1999 | Durance et al. | |
| 6,742,284 B2 | 6/2004 | Dinh | |
| 7,849,788 B2 | 12/2010 | Macaluso | |
| 9,066,910 B2 | 6/2015 | Rosenblatt et al. | |
| 9,687,027 B2 | 6/2017 | Poston et al. | |
| 10,143,706 B2 * | 12/2018 | Kotra | A61K 31/352 |
| 10,301,242 B2 * | 5/2019 | Zhang | C07C 37/82 |
| 2003/0150128 A1 | 8/2003 | Macaluso et al. | |
| 2004/0081577 A1 | 4/2004 | Macaluso et al. | |
| 2006/0034981 A1 | 2/2006 | Pan et al. | |
| 2011/0277337 A1 | 11/2011 | Ruden et al. | |
| 2013/0174438 A1 | 7/2013 | Moarn et al. | |
| 2015/0096189 A1 | 4/2015 | Hawes et al. | |
| 2017/0188623 A1 | 7/2017 | Cranford | |
| 2017/0218539 A1 | 8/2017 | Yoshida et al. | |

FOREIGN PATENT DOCUMENTS

| | | | | |
|---|---|---|---|---|
| CN | 106278828 A | * | 1/2017 | ............. C07C 37/82 |
| GB | 2400319 A | * | 10/2004 | ......... B01D 11/0242 |

OTHER PUBLICATIONS

Persechini, L., "Near-Infrared: A fact sheet," On Your Wavelength a physics blog from the Nature journals. (Year: 2018).*
McPartland J.M., McKernan K.J. (2017) Contaminants of Concern in Cannabis: Microbes, Heavy Metals and Pesticides. In: Chandra S., Lata H., El Sohly M. (eds) *Cannabis sativa* L.—Botany and Biotechnology. Springer, Cham. (Year: 2017).*
How to Quick-Dry Fresh-Off-The-Plant Cannabis, https://internationalhighlife.com/quick-dry-fresh-off-plant-cannabis/, Aug. 10, 2017, 13 pages.
Weeds that Please, Drying marijuana quickly. Fast and quick ways to dry your cannabis buds, www.weedsthatplease.com/quickdry.htm, Nov. 9, 2007, 2 pages.
Drying Your Weed—A Tutorial, 420 Magazine, https://www.420magazine.com/community/threads/drying-your-weed-a-tutorial.70414/, Nov. 6, 2007, 13 pages.

* cited by examiner

*Primary Examiner* — Michael Barker
(74) *Attorney, Agent, or Firm* — Hovey Williams LLP

(57) ABSTRACT

The present invention includes a method of drying *Cannabis* plant material generally comprising exposing the *Cannabis* plant material to infrared radiation emitted from an infrared heater, such as a catalytic gas heater, the radiation having a wavelength of from about 3 to about 10 microns; and heating the *Cannabis* plant material to a temperature of from about 100° F. to about 400° F.

27 Claims, 4 Drawing Sheets

METHODS OF HEATING CANNABIS PLANT MATERIAL

CROSS-REFERENCE TO RELATED APPLICATIONS

The present application claims the priority benefit of U.S. Provisional Application No. 62/693,651, filed Jul. 3, 2018, entitled METHODS OF HEATING *CANNABIS* PLANT MATERIAL, incorporated by reference in its entirety herein.

BACKGROUND

*Cannabis* plant material contains cannabinoid compounds that are useful in various applications, such as for pharmaceuticals, lotions, cancer treatment-related therapeutics, etc. However, like other plant materials, *Cannabis* plant material can be affected by mold, bacteria, and fungi, which may result in degradation of the cannabinoid compounds contained therein. Thus, preparing *Cannabis* plant material for use, storage, or extraction of the cannabinoid compounds often involves drying the plant material so as to preserve it for later use. Sanitation and sterilization of the *Cannabis* plant material is also desirable.

Present methods of drying *Cannabis* plant material involve hanging the plant in a humidity-controlled room, which takes a substantial amount of time, up to 14 days. Devices and methods have been contemplated to conduct this drying in much shorter time frames through heating of the material. However, caution must be exercised when applying heat to the *Cannabis* plant material as this can cause undesired, premature decarboxylation of the cannabinoid compounds contained therein, which can be highly undesirable in certain applications. However, in other applications, it can be desirable to cause the cannabinoid compounds to undergo decarboxylation thereby transforming the compounds into a more bioavailable form. But, exposure to high temperatures can cause degradation of the *Cannabis* plant material and other compounds contained therein, such as terpene compounds.

Therefore, it would be highly desirable for a drying system to be able to have the capability of drying while avoiding decarboxylation or causing decarboxylation of certain cannabinoid compounds within the plant material.

The background discussion is intended to provide information related to the present invention which is not necessarily prior art.

SUMMARY

The present invention solves the above-described problems and other problems by providing a distinct advance in the art of drying *Cannabis* plant material. More particularly, the present invention provides a method that enables rapid drying without undesired decarboxylation of cannabinoid compounds. The present invention also provides a method of decarboxylating cannabinoid compounds of *Cannabis* plant material without degradation of other components thereof. The present invention can also be used to sanitize or sterilize *Cannabis* plant material.

One embodiment of the present invention includes a method of drying a *Cannabis* plant material. The method broadly comprises exposing the *Cannabis* plant material to infrared radiation emitted from an infrared heater, the radiation having a wavelength of from about 3 to about 10 microns; and heating the *Cannabis* plant material to a temperature of from about 100° F. to about 400° F.

Another embodiment of the present invention includes a method of decarboxylating a cannabinoid compound contained within a *Cannabis* plant material. The method broadly comprises exposing the *Cannabis* plant material to infrared radiation emitted from an infrared heater, the radiation having a wavelength of from about 3 to about 10 microns; and heating the *Cannabis* plant material to a temperature of at least 200° F. for a sufficient time so as to decarboxylate at least 50% of the cannabinoid compound contained within the *Cannabis* plant material.

Another embodiment of the present invention includes a method of drying a *Cannabis* plant material while reducing the incidence of decarboxylation of a cannabinoid compound contained within the *Cannabis* plant material. The method broadly comprises exposing the *Cannabis* plant material to infrared radiation emitted from an infrared heater, the radiation having a wavelength of from about 3 to about 10 microns; and heating the *Cannabis* plant material to a temperature of from about 100° F. to about 160° F. to produce a dried *Cannabis* plant material, wherein the dried *Cannabis* plant material has a ratio of the cannabinoid compound to the decarboxyated cannabinoid compound of at least 2:1.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
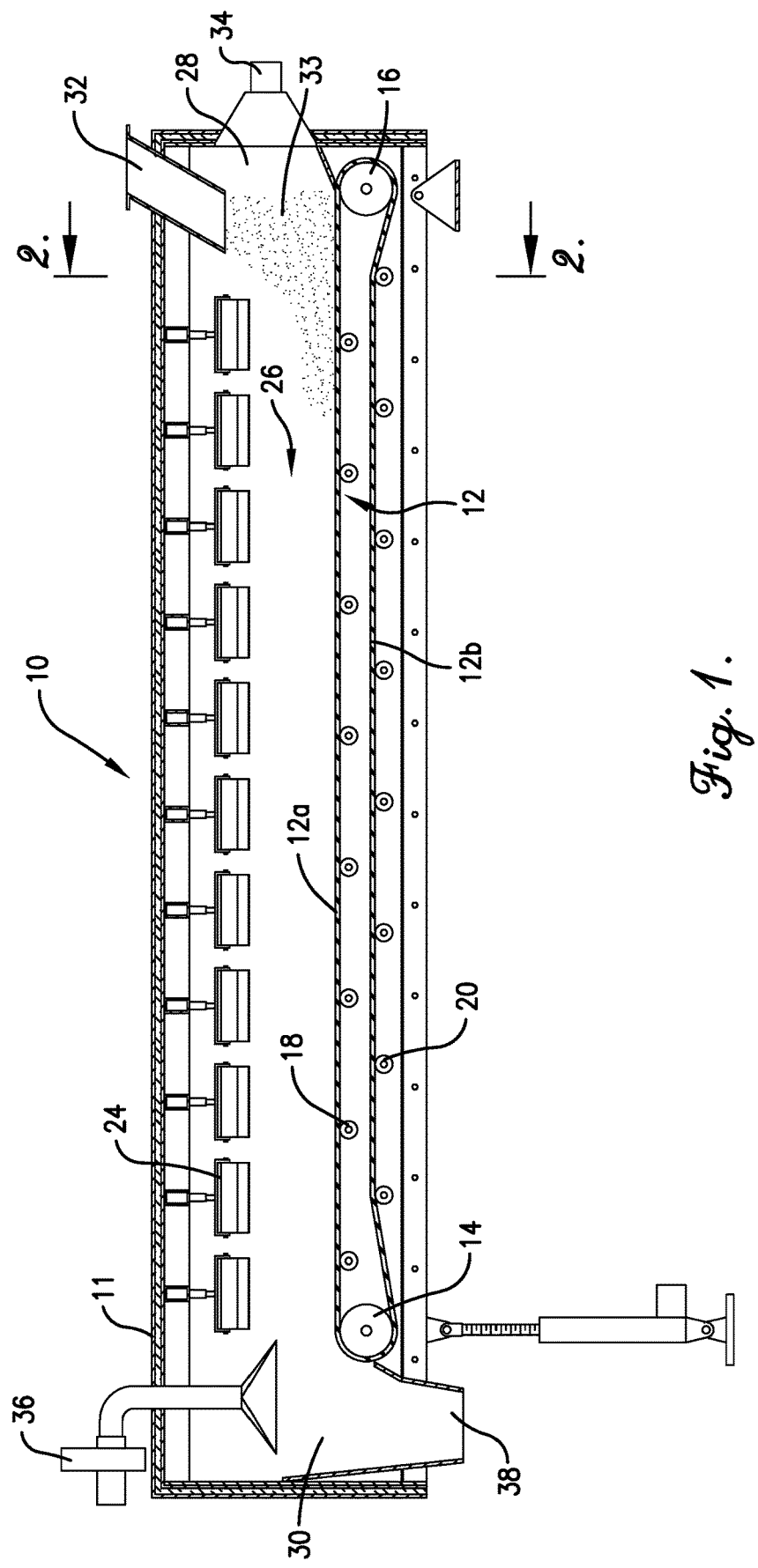
FIG. 1 is a schematic view of an infrared heating apparatus having a plurality of infrared heaters and a conveyor belt.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 2:
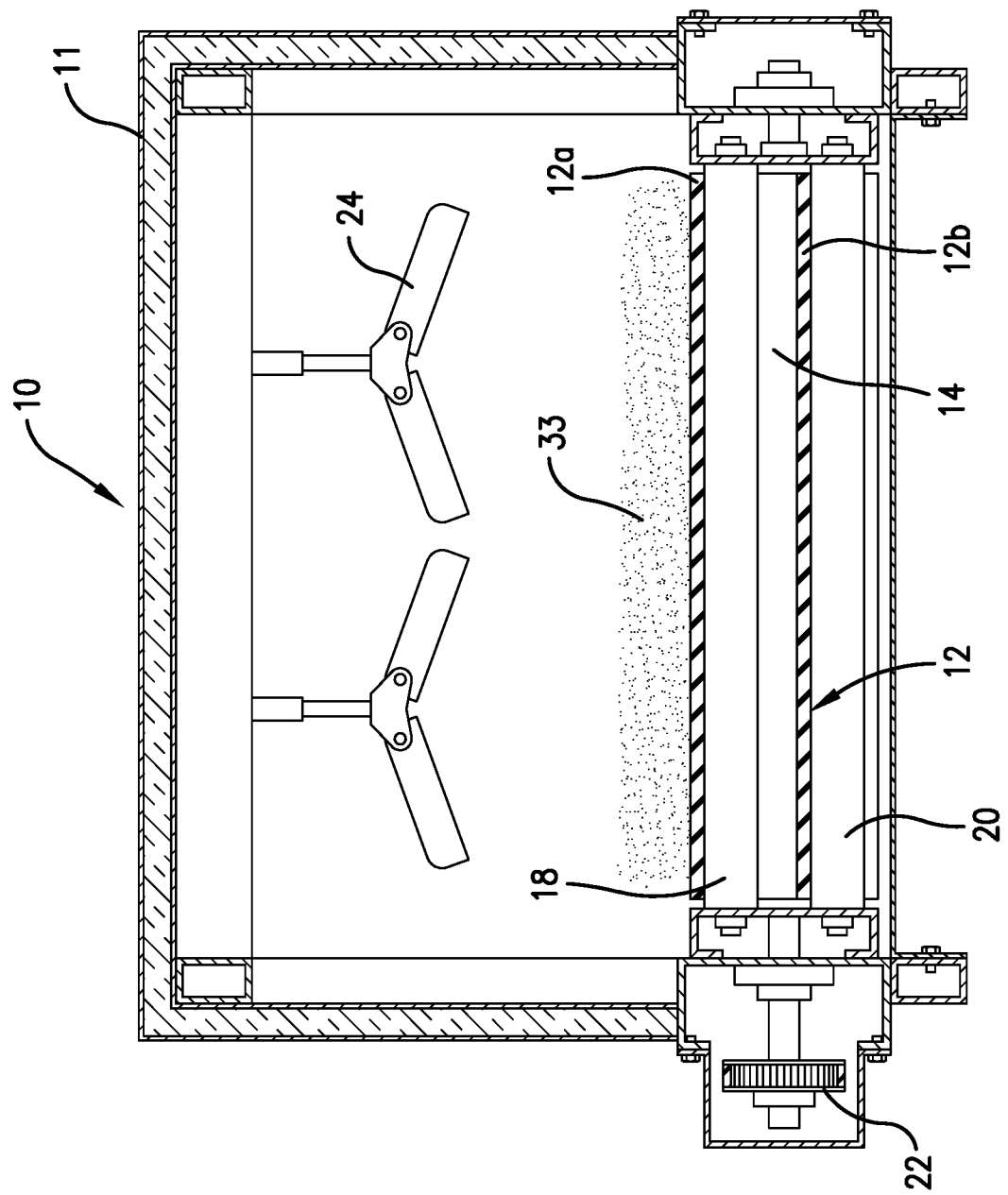
FIG. 2 is a side perspective view of the infrared heating apparatus of FIG.

Turning now to the drawing figures, and particularly FIG. 1, an infrared heating apparatus 10 useful for the present invention is illustrated. The heating apparatus 10 includes a housing 11 inside of which is located a continuous belt 12 oriented to present an upper run 12a and a lower run 12b. The belt 12 is supported at respective ends by rollers 14 and 16 and by a plurality of spaced-apart upper rollers 18 and lower rollers 20. As shown in FIG. 2, a driving means 22, such as a motor drive, may spin one of the rollers 14, 16, which drives the belt 12, The heating apparatus 10 includes a bank of infrared heaters 24. The heaters 24 are arranged in facing relationship to the belt 12 so that infrared energy emitted from heaters 24 is directed toward belt 12. Housing 11 defines an elongated passageway 26 that is coextensive with the bank of heaters 24 and belt 12. Passageway 26 comprises a product inlet end 28 and a product outlet end 30. Infrared heaters 24 may comprise flameless catalytic gas heaters such as those available from Catalytic Industrial Group, Independence, Kans. In certain embodiment, other infrared emitter technology can be used, including electric heaters and other similar alternatives. The heaters 24 preferably emit infrared radiation within a wavelength spectrum of about 3 to about 10 microns, more preferably about 3 to about 7 microns, which encompasses a preferred absorption spectrum for water in its liquid state. As illustrated, the upper run 12a of belt 12 extends along substantially the entire length of passageway 26.

The heating apparatus 10 includes a product inlet 32, for example, a chute, adjacent inlet end 28, for the purpose of directing Cannabis plant material 33 into housing 11 and depositing it onto the upper surface of belt run 12a. Although not shown, the product inlet 32 may be equipped with a rotary valve or other conventional device for depositing a relatively even layer of Cannabis plant material 33 onto run 12a during movement thereof. As used herein, "Cannabis plant material" can mean the entire plant of a member of the Cannabis plant family (e.g., Cannabis indica, Cannabis Sativa, or Cannabis ruderalis) or any portion thereof such as the leaves, stalks, buds, or kief.

In certain embodiments, the Cannabis plant material may be water cured (not shown) prior to introduction to heating or introduction into heating apparatus 10. Water curing refers to a pre-treatment process where the Cannabis plant material is soaked in water (for example, for about 1 to about 10 hours, or about 3 to 8 hours) prior to the drying process. This pre-treatment can help reduce the length of the drying cycle that is typically needed. It can also help remove the undesirable, grassy aftertaste in the dried Cannabis product.

The heating apparatus 10 further includes air circulators 34, 36. The air circulators 34, 36 may be electric fans, inlets from external fans, combustion-powered blowers, or any type of air circulation device known in the art. Air circulators 34 cause a flow of air through the passageway 26 as the Cannabis plant material 33 travels therethrough thereby facilitating convective heat transfer between the infrared heaters 24 and the Cannabis plant material 33. Air circulator 36 assists with further drying of Cannabis plant material 33 falling off belt 12 through a dried product outlet 38, which again may be in the form of a chute.

In operation, Cannabis plant material 33 to be treated is admitted to apparatus 10 via product inlet 32 and is in turn placed upon the upper surface of belt run 12a. As the belt 12 is moved, the deposited Cannabis plant material 33 is conveyed through passageway 26 where it is exposed to infrared energy emitted by the plurality of infrared heaters 24. After sufficient exposure to infrared energy, which is discussed further below, the treated Cannabis plant material 33 falls under the influence of gravity from belt run 12a adjacent product outlet end 30, and then may be conventionally collected on by a cooling belt or bin (not shown).

Figure 3:
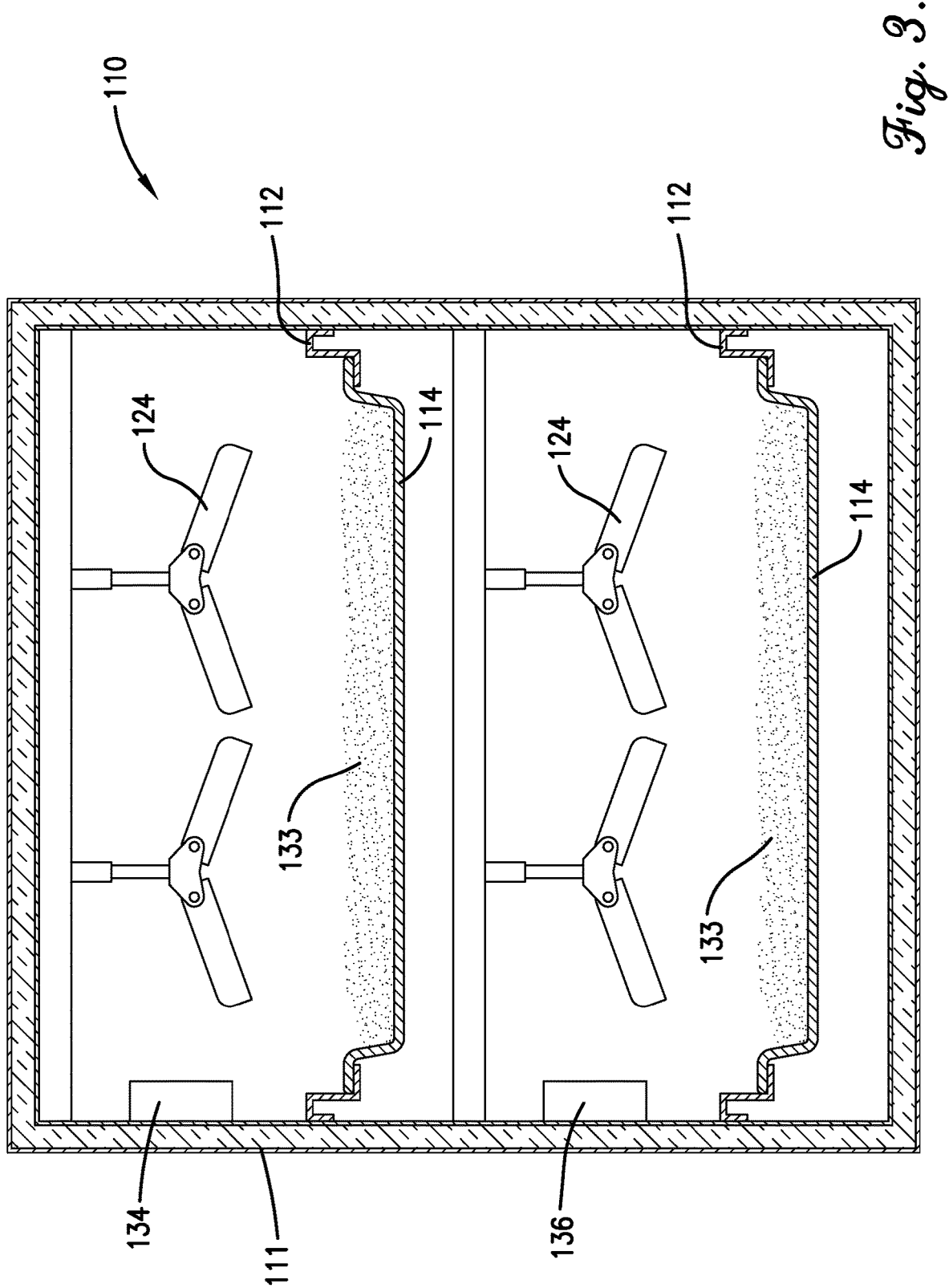
FIG. 3 is a schematic view of an infrared heating apparatus having a plurality of infrared heaters and pull-out trays.

FIG. 3 depicts another heating apparatus 110 useful for the present invention. Heating apparatus 110 is a batch-wise heater, as opposed to the continuous heater 10 of the previous embodiment. Apparatus 110 may be more useful and efficient in processing smaller quantities of material than apparatus 10. The heating apparatus 110 comprises a housing 111 to which are secured a plurality of shelve guides 112 that may receive removable trays 114. The trays 114 are used for holding the Cannabis plant material 133 thereon. A bank of heaters 124 is positioned above each tray 114 for exposing the Cannabis plant material 133 to infrared energy. The heaters 124 may be comprised of the same kind of catalytic gas heaters discussed above. The heating apparatus 110 may also include air circulators 134, 136, which aid convective heat transfer between the heaters 124 and the material 133.

In operation, Cannabis plant material 133 to be treated is deposited on the trays 114, which are then placed on their respective shelve guides 112. The heaters 124 then expose the Cannabis plant material 133 on the trays 114 to infrared radiation. Once the Cannabis plant material 133 is sufficiently processed, the trays 114 may be removed from the shelve guides 112 and the material 133 recovered therefrom.

Figure 4:
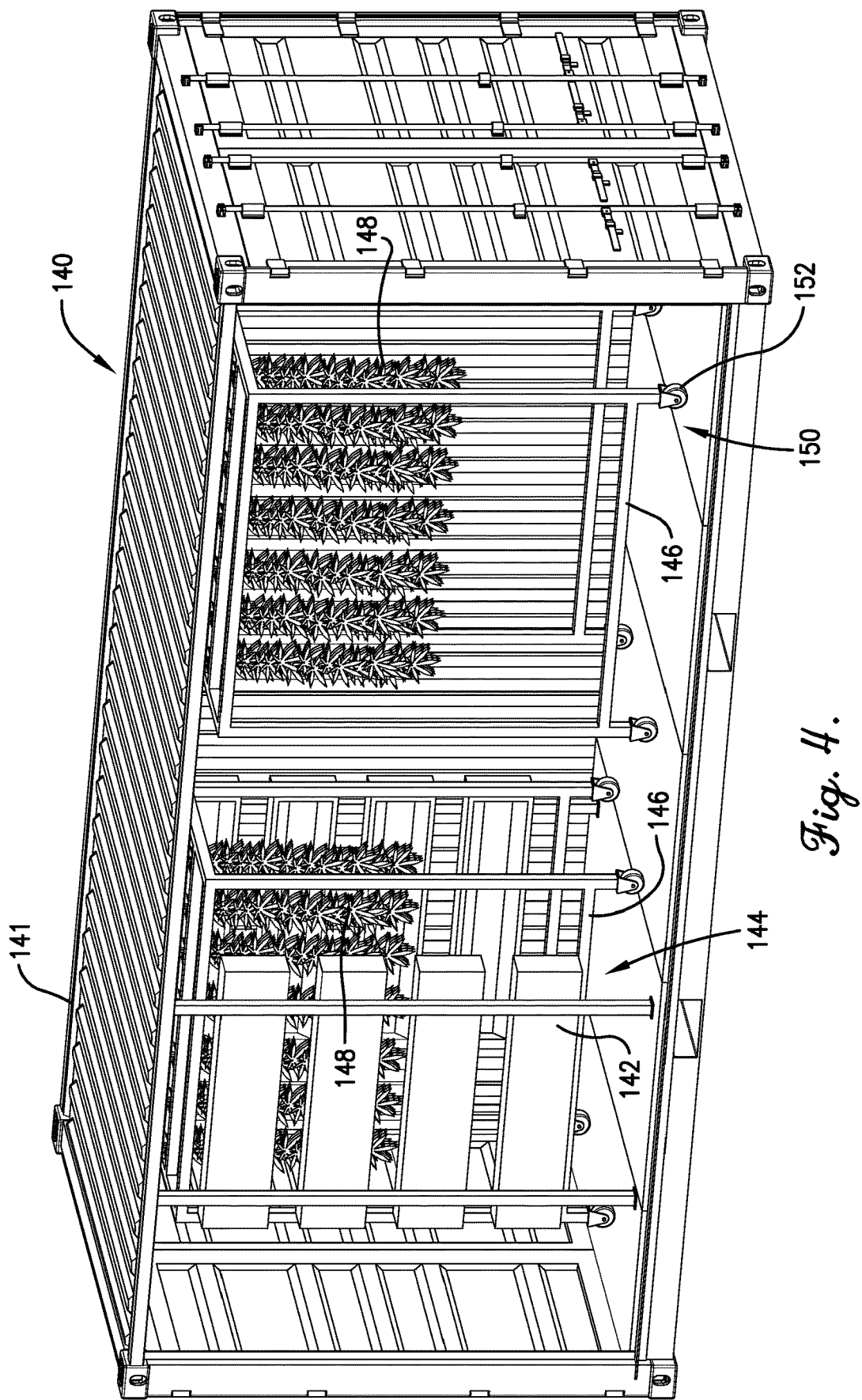
FIG. 4 is a schematic view of a heating apparatus for use with an embodiment of the present invention in which trays containing the plant material can be transferred between heating sections for drying under different temperature conditions.

FIG. 4 depicts a heating apparatus 140 comprising a plurality of heating elements 142 located within a first drying section 144. The heating elements 142 may be comprised of the same kind of catalytic gas heaters discussed above. The heating apparatus 140 may comprise a modified shipping container 141, or other suitable housing, and is configured to receive one or more removable trays 146 that are configured to hold the plant material 148 thereon. In addition to first drying section 144, apparatus 140 comprises at least one other drying section 150. In the illustrated embodiment, heating elements 142 are located in only the first drying section 144. However, other configurations are possible without departing from the scope of the present invention. For example, the heating apparatus may comprise a plurality of drying sections 144, 150. In such embodiments, at least one of the drying sections 150 should not comprise any heating elements 142 that would directly irradiate plant material 148 carried by tray 146. Instead, the plant material 148 located within drying section 150 would be dried via convective heat that originated within a drying section 144. The avoidance of placing heating elements in each drying section permits creation of temperature gradients within apparatus 140. The heating elements 142 may be arranged on one wall of container 140, or may be arranged on two facing walls of apparatus 140, as illustrated.

In this embodiment, by placing heating elements 142 in fewer than all drying section, a temperature gradient is produced within the heating apparatus 140 so that the more moist material is exposed to higher temperatures so as to drive off moisture quickly. Then, as the moisture content decreases, the plant material is moved into cooler drying sections, so that additional moisture can be removed without subjecting the plant material to as intense of heat, which may lead to the decarboxylation of various cannabinoid compounds. As illustrated, the removable trays 146 comprise rollers 152 to facilitate shifting of the trays between drying sections 144 and 150. It will be appreciated that a number of mechanisms can be employed in order to index the trays 146 within apparatus 140. These include both manual and automated systems such as rail/track systems, chain or belt-drive conveyor systems, and the like. Several modifications of this concept from what is illustrated are possible and are within the scope of the present invention. For instance, heating elements 142 may be located in multiple drying sections 144, but not present in at least one other drying section 150. The energy delivered from heating elements 142 in adjacent drying sections can be adjusted so that the temperature is greatest in the first drying section, and then declines as the plant material is moved to downstream drying sections.

In certain embodiments, heating apparatuses 10, 110, 140 can include a condenser (not shown) operable to condense water and other volatilized components from the *Cannabis* plant material. For example, during the drying process, terpenes can be volatilized along with water. These components can be condensed, along with any other volatilized solvents and components, and the terpenes can be extracted from the condensed liquid as a valuable by-product of the drying process, The manner in which heating apparatuses 10, 110, 140 are operated depend largely upon the desired outcome of the processing. In one embodiment, the desired outcome may be to dry the *Cannabis* plant material while avoiding decarboxylation of cannabinoid compounds contained within the material. It has been discovered that exposing the *Cannabis* plant material to infrared radiation from catalytic gas heaters at a wavelength of from about 3 to about 10 microns, preferably 3 to 7 microns will rapidly reduce the moisture content while also avoiding undesired decarboxylation of cannabinoid compounds and degradation of terpenes and/or trichomes within the *Cannabis* plant material. In such embodiments, the plant material is heated to a maximum temperature of from about 100° F. to about 180° F., preferably of from about 165° F. to about 175° F. for a period of time of no more than 2 hours, nor more than 1.5 hours, no more than 1 hour, or more than 45 minutes. Alternatively, the period over which the heating occurs is from about 10 minutes to about 1.5 hours, about 20 minutes to about 1 hour, or about 30 minutes to about 45 minutes. In another aspect, the gas pressure of the catalytic gas heaters, when fueled with propane, may be about 7 inches water column up to about 10 inches water column. It is understood that other fuels, such as natural gas and liquefied petroleum gas (LPG) (including butane and propane mixtures), may be used to fuel the heaters; however, the pressures employed will be adjusted to account for different energy content of the fuel. In other embodiments, the heaters are operated at a gas pressure that permits the heater output to vary from 50% to 100% of the heater's rated power, In certain embodiments, the *Cannabis* plant material is heated while in a cool or refrigerated environment. For example, housing 11, 111, or 141 may include a refrigeration unit (not shown). In certain embodiments, the drying process comprises maintaining the temperature in the environment around the plant material and heaters at a temperature below about 70° F., about 60° F., about 50° F., or about 40° F. In such embodiments, the plant material is heated to a temperature of from about 100° F. to about 180° F., preferably of from about 110° F. to about 130° F. for the heating duration. Drying the plant material in such a cool or refrigerated environment can result in a number of advantageous properties in the *Cannabis* product. For example, maintaining the cool or refrigerated environment enables better temperature control, which can reduce the loss of terpenes in the *Cannabis* plant material, Additionally, the cool or refrigerated environment allows for a more rapid decrease in temperature of the plant material when the heaters are turned off, for example in a cooling or tempering step (described below).

In certain embodiments, a tempering step can be included to cool down the plant material between heating steps. Such a tempering step prevents the temperature of the plant material from rising too fast, which unexpectedly resulted in improved preservation of terpenes within the plant material. In certain embodiments, such a tempering/cooling step is critical to achieving a high-quality *Cannabis* product. In certain embodiments, the drying process may comprise more one, two, three, or more tempering steps between heating steps. The tempering can be performed at room temperature, for example by turning off the heaters, moving the heaters away from the plant material, and/or moving the plant material away from the heaters, or at refrigerated temperatures as explained above. In certain embodiments, the tempering comprises cooling the plant material to a temperature of from about 40° F. to about 90° F., preferably of from about 50° F. to about 80° F. In certain embodiments, the plant material is cooled for a period of time of about 1 to about 24 hours, preferably about 2 to about 12 hours. In particularly preferred embodiments, the drying process comprises heating the plant material for about 1 to about 8 hours, preferably about 2 to about 6 hours, followed by tempering/cooling for about 1 to about 12 hours, preferably about 2 to about 8 hours, followed by heating (re-heating) for about 1 to about 8 hours, preferably about 2 to about 6 hours. The heating and tempering times can be selected as necessary depending the conditions of the *Cannabis* plant material being dried, including stem, leaves, and flower content, as well as moisture content (for example, from water curing step).

In certain embodiments, exposure of the *Cannabis* plant material to the infrared radiation emitted from the catalytic heaters also results in a reduction of moisture within the material. In particular, the plant material can be dried to a moisture content of less than 20% by weight, less than 15% by weight, or less than 10% by weight. In another aspect, the percentage of weight loss due to water content evaporation during exposure is at least 5%, at least 7.5%, or at least 10%, all while avoiding undesired decarboxylation of at least one cannabinoid compound contained in the *Cannabis* plant material. In particular embodiments, processing of the plant material within a heating apparatus according to the present invention reduces the moisture content of the plant material, as compared to its moisture content immediately prior to being introduced into the heating apparatus, by at least 50%, by at least 60%, or by at least 70% by weight.

Particularly, the loss of carboxylated cannabinoid compounds, when measured in comparison to the starting plant material prior to exposure to the infrared radiation emitted by the catalytic heaters, is less than 25%, less than 20%, less than 15%, or less than 10% by weight. Stated differently, less than 25%, less than 20%, less than 15%, or less than 10% of the cannabinoid compounds in the *Cannabis* plant material is decarboxylated after exposure of the *Cannabis* plant material to the infrared radiation emitted from the catalytic gas heaters. In another aspect, the dried *Cannabis* plant material may have a ratio of the cannabinoid compound to the decarboxylated cannabinoid of at least 2:1, at least 3:1, at least 4:1, or at least 9:1.

Generally, the most desired cannabinoid compounds within the *Cannabis* plant material are cannabidiolic acid (CBDA) and/or tetrahydrocannabinolic acid (THCA), which may be decarboxylated into cannabidiol (CBD) and tetrahydrocannabinol (THC), respectively. In certain embodiments, the drying of the *Cannabis* plant material does not require or utilize any kind of active humidity control measures. By "active humidity control measures," it is meant any direct actions whose primary purpose is to control the relative humidity of the environment under which drying of the *Cannabis* plant materials is occurring. However, active humidity control measures may also be used in accordance with embodiments of the present invention. In other embodiments, it may also be desirable to dry the *Cannabis* plant material while using air circulation so as to increase convective heat transfer and speed the drying process, although such is not essential.

In another embodiment, the focus in drying the *Cannabis* plant material may be to decarboxylate a significant portion of at least one cannabinoid compound (e.g., CBDA or THCA) contained therein. Decarboxylating the cannabinoid compound transforms it into a bioavailable form (e.g., CBD or THC), thereby permitting those compounds to be formulated into products such as lotions and oils. Further, it has been discovered that exposing the *Cannabis* plant material to infrared radiation from catalytic gas heaters will very effectively and efficiently decarboxylate the cannabinoid compound without an appreciable loss of terpene content. Generally, such terpene content loss can be kept below 10%, 5%, or 1% by weight.

In embodiments in which decarboxylation is a desired outcome, the *Cannabis* plant material is heated to a temperature of from about 200° F. to about 400° F., or from about 250° F. to about 375° F., or from about 300° F. to about 350° F., for a period of time of less than 30 minutes, less than 20 minutes, or less than 10 minutes. In preferred embodiments, the *Cannabis* plant material is heated to a temperature of at least about 285° F., at least about 300° F., at least about 325° F., or at least about 350° F. during the heating step. In some embodiments, the *Cannabis* plant material may be shredded prior to exposure. Alternatively, the heating step is conducted for a period of about 1 to about 10 minutes, or about 2 to about 5 minutes. In another aspect, the catalytic gas heaters, when fueled with propane, may operate at a gas pressure of at least 10.5 inches of water column up to about 11 inches of water column. In addition, air circulation and active humidity control is not required to achieve decarboxylation of the cannabinoid compound. In another aspect, at least 50%, at least 60%, at least 70%, or at least 75% of the cannabinoid compounds in the *Cannabis* plant material is decarboxylated after exposure of the *Cannabis* plant material to the infrared radiation emitted from the catalytic gas heaters.

The methods in accordance with embodiments of the present invention have a number of advantages over prior art methods. For example, freshly harvested *Cannabis* plant material can be dried to less than 15% moisture level in as little as about 1.5 hours, about 1 hour, about 30 minutes, or about 15 minutes, and water cured *Cannabis* plant material can be dried in as little as about 1.75 hours, while traditional drying methods can vary between 7 to 14 days. Additionally, embodiments of the present invention can be used to sanitize and sterilize *Cannabis* plant material, for example by killing unwanted insects, larvae, and eggs in the material and/or reducing the levels of microbes to acceptable limits. In certain embodiments, the methods are capable of reducing the levels of *E. Coli, Salmonella*, Aflatoxin, and/or Ochratoxin below the detectable limits. In certain embodiments, the methods are capable of reducing the levels of Enterobacterlaceae below 20 CFU/g, well below the allowable limit of 10,000 CFU/g, The following examples set forth illustrative methods in accordance with the invention, describing techniques for drying *Cannabis* plant material and decarboxylating cannabinoid compounds contained within *Cannabis* plant material. It is to be understood, however, that these examples are provided by way of illustration only, and nothing in them should be taken as a limitation upon the overall scope of the invention.

Example 1

In this example, samples of *Cannabis* plant material were dried using catalytic gas heaters fueled by propane, Although, it is understood that natural gas could also be used to fuel the heaters. Thereafter, the degree of decarboxylation and moisture content loss were recorded.

A sample of *Cannabis* plant material was obtained, chopped, and ground. The mass of the sample was weighed, and the moisture content thereof was measured. Catalytic infrared gas heaters within a chamber were preheated with the gas pressure being at 9 to 11 inches of water column. The samples of *Cannabis* plant material were positioned 12 inches below the catalytic gas heaters in the chamber with air circulation flowing within the chamber for some sample sets. The *Cannabis* plant material was then exposed to the infrared radiation of the catalytic gas heaters for a period of time.

Once the period of time had expired, the *Cannabis* plant material's temperature was recorded, and the plant material was removed. The decarboxylation levels of the cannabinoid compound were recorded along with the moisture content, The following tables set forth the parameters of the infrared heating tests using the five 250 g samples, as well as results for moisture content and decarboxylation levels.

TABLE 1.1

| Sample Number | Mass (g) | Window (Inches) | Gas (Inches) | Air Circulation | Time Heated (Minutes) | Temperature of Plant Material (° F.) |
|---|---|---|---|---|---|---|
| 1 | 250 | 12 | 11 | off | 14 | 280 |
| 2 | 250 | 12 | 9 | on | 20 | 185 |
| 3 | 250 | 12 | 9 | on | 35 | 173 |
| 4 | 250 | 12 | 9 | on | 30 | 175 |
| 5 | 250 | 12 | 11 | on | 24 | 295 |

TABLE 1.2

| Sample Number | % Decarboxylation | % Loss due to Moisture Content | Standard Deviation | % Relative Standard Deviation |
|---|---|---|---|---|
| 1 | 28.8% | 6.06% | 0.29% | 4.86% |
| 2 | 12.4% | 9.92% | 1.04% | 10.44% |
| 3 | 4.29% | 10.5% | 1.28% | 12.18% |
| 4 | 6.28% | 11.4% | 0.28% | 2.48% |
| 5 | 64.1% | 0.77% | 0.22% | 28.60% |

TABLE 1.3

| Sample Number | CBDA (mg/g) | CBD (mg/g) | CBDA (% w/w) | CBD (% w/w) | Total CBD, adjusted (mg/g) |
|---|---|---|---|---|---|
| 1 | 4.04 | 1.73 | 0.40% | 0.17% | 5.27 |
| 2 | 14.36 | 2.07 | 1.44% | 0.21% | 14.66 |
| 3 | 14.19 | 0.64 | 1.42% | 0.06% | 13.08 |
| 4 | 10.49 | 0.71 | 1.05% | 0.07% | 9.91 |
| 5 | 3.44 | 8.19 | 0.34% | 0.82% | 11.21 |

Tables 1.1 through 1.3 demonstrate that when exposed to the catalytic gas heaters, the *Cannabis* plant material generally experienced more moisture loss with less decarboxylation of cannabinoid compounds when the temperature of the plant material did not exceed 185° F., when the catalytic gas heater was operated using propane at a pressure of about 9 inches of water column, and when the air circulation was on. These results indicate that when using an embodiment of the present invention, the *Cannabis* plant material may be substantially dried in under 35 minutes without decarboxylating a majority of the cannabinoid compounds of the *Cannabis* plant material and without requiring humidity control.

Example 2

In this example, samples of *Cannabis* plant material were dried using the prior art process of drying in a humidity-controlled room, and then the dried *Cannabis* plant material was exposed to infrared radiation so that cannabinoid compounds within the *Cannabis* plant material were decarboxylated. Thereafter, the degree of decarboxylation and moisture content loss were recorded.

A sample of *Cannabis* plant material was obtained, chopped, ground, and dried. The mass of the sample was weighed, and the moisture content thereof was measured. Catalytic infrared gas heaters within a chamber were preheated with the gas pressure being at 11 inches of water column. The samples of *Cannabis* plant material were positioned 6 or 12 inches below the catalytic gas heaters in the chamber without air circulation flowing within the chamber. The *Cannabis* plant material was then exposed to the infrared radiation of the catalytic gas heaters for a period of time, Once the period of time had expired, the *Cannabis* plant material's temperature was recorded, and the plant material was removed. The decarboxylation levels of the cannabinoid compound were recorded along with the moisture content.

The following tables set forth the parameters of the infrared heating tests using the seven 80 g samples, as well as results for moisture content and decarboxylation levels.

TABLE 2.1

| Sample Number | Mass (g) | Window (Inches) | Gas (Inches) | Air Circulation | Time Heated (Minutes) | Temperature of Plant Material (° F.) |
|---|---|---|---|---|---|---|
| 1 | 80 | 6 | 11 | off | 1 | 335 |
| 2 | 80 | 6 | 11 | off | 0.5 | 295 |
| 3 | 80 | 12 | 11 | off | 1 | 270 |
| 4 | 80 | 12 | 11 | off | 1.5 | 300 |
| 5 | 80 | 12 | 11 | off | 2 | 315 |
| 6 | 80 | 12 | 11 | off | 0.5 | 240 |
| 7 | 80 | 12 | 11 | off | 3 | 350 |
| 8 | 80 | 12 | 11 | off | 4 | — |

TABLE 2.2

| Sample Number | % Decarboxylation | % Loss due to Moisture Content | Standard Deviation | % Relative Standard Deviation |
|---|---|---|---|---|
| 1 | 48.3% | 1.30% | 0.22% | 16.99% |
| 2 | 35.4% | 3.28% | 0.17% | 5.09% |
| 3 | 34.0% | 2.26% | 0.13% | 5.54% |
| 4 | 46.4% | 1.32% | 0.18% | 13.23% |
| 5 | 58.7% | 0.85% | 0.10% | 12.03% |
| 6 | 25.0% | 3.80% | 0.13% | 3.45% |
| 7 | 80.7% | 0.35% | 0.02% | 6.66% |
| 8 | >95% | — | — | — |

TABLE 2.3

| Sample Number | CBDA (mg/g) | CBD (mg/g) | CBDA (%w/w) | CBD (%w/w) | Total CBD, adjusted (mg/g) |
|---|---|---|---|---|---|
| 1 | 20.2 | 21.7 | 2.02% | 2.17% | 39.42 |
| 2 | 27.61 | 16.41 | 2.76% | 1.64% | 40.63 |
| 3 | 24.53 | 13.61 | 2.45% | 1.36% | 35.12 |
| 4 | 20.56 | 20.28 | 2.06% | 2.03% | 38.31 |
| 5 | 12.36 | 21.94 | 1.24% | 2.19% | 32.78 |
| 6 | 31.82 | 11.13 | 3.18% | 1.11% | 39.05 |
| 7 | 3.4 | 34.23 | 0.34% | 3.42% | 37.21 |

Tables 2.1 through 2.3 demonstrate that when exposed to the catalytic gas heaters, the greater the temperature of the plant material, the greater the level of decarboxylation of the cannabinoid compounds that is achieved. In particular, the greatest level of decarboxylation was found to occur when the temperature of the *Cannabis* plant material reached about 350° F. The results further indicate that when using an embodiment of the present invention, substantial decarboxylation of the cannabinoid compounds can be achieved very quickly, namely in under about 3.5 minutes.

Example 3

Samples were provided to the test site (Praxis Laboratory Lab #0020) to be processed and tested as described below.

The test site was provided a heating apparatus in accordance with one embodiment of the present invention. The apparatus comprised a single 12" by 12" Catalytic heater panel mounted vertically facing the plants. A "wave" guide that is about 12" by 4" was mounted around the heater to help focus the infrared energy towards the sample instead of towards the sides. The drying area was 24" by 24" and had a mesh screen that allowed products to be hung. This embodiment allows the user to dry the samples before any trimming is performed. The plants were cut with all stems, leaves, and flowers still attached. This is known as dry trimming, where the plants are normally hung up to dry before any trimming is done (as opposed to wet trimming, where the flowers are cut off the plant soon after the plant is cut and then only the flowers with small leaves are dried).

The apparatus operated with LPG with a supply pressure of 11 inches of water column for high fire operation. Given that keeping temperature under control was a concern, it is estimated that the unit could run at a lower pressure (less heat) to shorten the distance from the heater to make the unit smaller. There was no air circulation other than what movement caused by personnel moving about.

The test site hung samples at 24" to 30" away from the heater panel. The samples were eventually moved to about 48" away to keep the temperature low (around 100 F). Based on previous testing from the wet trimmed test site, it was expected that dry trimming would take longer to dry as there are a lot more mass. Instead of only the flowers with some small leaves, all the leaves with all the stems would all need to be dried. It was expected to take at least 4 hours of heat (2 hours on, 2 hours temper, 2 more hours of heat), and likely 6 or more hours of total heating time to dry the samples given the heavier mass content. This was exactly the case.

The samples were dried with exposure to the heaters for a total of 9 hours over the span of two days. On the first day, the samples were exposed for 6 hours, with the samples being turned every hour as the heat was only from 1 side. After 6 hours, the heaters were turned off and the samples hung overnight with no heat. On the morning of the second day, the samples were heated for an additional 3 hours, again turning the samples every hour, until the samples were satisfactorily dried.

The resulting samples were lab tested, with the results shown in the tables below. Notably, the lab indicated that the THC content of 25% was consistent with the typical air dried "good" products. This evidences that the embodiment of the present invention does not negatively impact the THC level. Furthermore, the biological and toxin test showed that this sample passed those tests. Lab testing of dried product showed no detectable amount of *E. Coli*, *Salmonella*, Aflatoxin, and Ochratoxin. Trace amounts (<20 CFU/g) of Enterobacterlaceae was detected, but under the passing limit of <10,000 CFU/g.

It has also been found that heating from both sides to makes the process more effective, so embodiments of the invention include an apparatus having heaters on both sides of the samples being dried.

TABLE 3.1

Cannabinoid Concentration Analysis - Method: HPLC

| Component | Result (%) |
| --- | --- |
| CBC | <0.01 |
| CBCA | <0.01 |
| CBD | <0.01 |
| CBDA | <0.01 |
| CBDV | <0.01 |
| CBDVA | <0.01 |
| CBG | <0.01 |
| CBGA | 0.46 |
| CBL | <0.01 |
| CBN | <0.01 |
| CBNA | 0.23 |
| THCA | 24.07 |
| THCV | <0.01 |
| THCVA | 0.25 |
| Δ-8 THC | <0.01 |
| Δ-9 THC | 0.59 |
| Total THC[1] | 21.71 |
| Total CBD[2] | <0.01 |
| Total Cannabinoids[3] | 25.61 |

[1]Total THC = THCA × 0.877 + Δ-9 THC
[2]Total CBD = CBDA × 0.877 + CBD
[3]Sum of all cannabinoids without conversion factor applied to THCA or CBDA

TABLE 3.2

Foreign Matter Screening - Method: Visual/Microscopy

| Component | Result (%) | WSLCB Limit | Pass/Fail |
| --- | --- | --- | --- |
| Stems | nd | <5 | Pass |
| Seeds | nd | <2 | Pass |
| Other | nd | <2 | Pass |

TABLE 3.3

Water Activity Analysis - Method: Hygrometer

| | Result (aW) | WSLCB Limit | Pass/Fail |
| --- | --- | --- | --- |
| Water Activity | 0.42 | <0.65 | Pass |

TABLE 3.4

Moisture Content Analysis - Method: Gravimetric

| | Result (%) | WSLCB Limit | Pass/Fail |
| --- | --- | --- | --- |
| Moisture Content | 8.98 | <15 | Pass |

TABLE 3.5

Terpene Concentration Analysis - Method: GC-FID

| Component | Result (%) |
| --- | --- |
| Alpha-Bisabolol | 0.11 |
| Alpha-Humulene | 0.13 |
| Alpha-Pinene | 0.11 |
| Alpha-Terpinene | nd |
| Alpha-Terpineol | n/a |
| Beta-Caryophyllene | 0.46 |

TABLE 3.5-continued

Terpene Concentration Analysis - Method: GC-FID

| Component | Result (%) |
|---|---|
| Beta-Myrcene | 0.02 |
| Beta-Pinene | 0.11 |
| Borneol | n/a |
| Camphene | 0.01 |
| Citral | n/a |
| Citronellol | n/a |
| Delta-3-Carene | nd |
| Dihydrocarveol | n/a |
| D-Limonene | 0.24 |
| Fenchone | n/a |
| Gamma-Terpinene | nd |
| Geraniol | nd |
| Guaiol | nd |
| Isopulegol | 0.03 |
| Linalool | 0.11 |
| Nerolidol | 0.56 |
| Ocimene | nd |
| P-Cymene | nd |
| Pulegone | n/a |
| Terpinolene | nd |
| 2-Piperidinone | n/a |
| Total Terpenes | 1.89 |

TABLE 3.6

Microbiological Screening - Method: FDA BAM

| Microbe | Result (CFU/g) | WSLCB Limit | Pass/Fail |
|---|---|---|---|
| Enterobacterlaceae | <20 | <10,000 | Pass |
| E. Coli | nd | * | Pass |
| Salmonella | nd | * | Pass |

* Not detected in 1 gram.

TABLE 3.7

Mycotoxin Screening - Method: ELISA

| Toxin | Result (ppb) | WSLCB Limit | Pass/Fail |
|---|---|---|---|
| Aflatoxin | nd | <20 | Pass |
| Ochratoxin | nd | <20 | Pass |

TABLE 3.8

Residual Solvent Screening - Method: GC-FID HS-FET

| Solvent | Result (ppm) | WSLCB Limit | Pass/Fail |
|---|---|---|---|
| Acetone | n/a | 5,000 | n/a |
| Benzene | n/a | 2 | n/a |
| Butanes | n/a | 5,000 | n/a |
| Chloroform | n/a | 2 | n/a |
| Cyclohexane | n/a | 3,880 | n/a |
| Dichloromethane | n/a | 600 | n/a |
| Ethanol | n/a | n/a | n/a |
| Ethyl Acetate | n/a | 5,000 | n/a |
| Heptanes | n/a | 5,000 | n/a |
| Hexanes | n/a | 290 | n/a |
| Isopropanol | n/a | 5,000 | n/a |
| Methanol | n/a | 3,000 | n/a |
| Pentanes | n/a | 5,000 | n/a |
| Propane | n/a | 5,000 | n/a |
| Toluene | n/a | 890 | n/a |
| Total Xylene | n/a | 2,170 | n/a |

Example 4

Samples of immature *Cannabis* plant leaves with very little stems were dried. A CENCO moisture balance was used in the testing. It uses an electric infrared heat lamp to put IR on the product in the scale pan. The device includes a rheostat to adjust the power to the lamp that has a graduated scale from 0 to 120. The ambient outside temperature during the testing was constant at 89° F.

In the first test, the rheostat was set to 60. An infrared thermometer was used to measure the temperature of the plant material being dried.

TABLE 4.1

| Time (m) | Temp (F.) | Loss in Weight Reading % | Weight Remaining % | Water Weight % of Total Mass | Moisture Content (Calculated) % Dry Basis | Moisture Content (Calculated) % Wet Basis |
|---|---|---|---|---|---|---|
| 0 | 83.8 | 0.0 | 100.0 | 72.5 | 298.18% | 72.50% |
| 1 | — | 1.6 | 98.4 | 70.9 | 292.36% | 72.05% |
| 2 | — | 5.4 | 94.6 | 67.1 | 278.55% | 70.93% |
| 3 | 135.5 | 8.4 | 91.6 | 64.1 | 267.64% | 69.98% |
| 4 | — | 13.0 | 87.0 | 59.5 | 250.91% | 68.39% |
| 5 | 137.1 | 16.5 | 83.5 | 56.0 | 238.18% | 67.07% |
| 6 | 137.1 | 21.5 | 78.5 | 51.0 | 220.00% | 64.97% |
| 7 | 134.2 | 26.0 | 74.0 | 46.5 | 203.64% | 62.84% |
| 8 | 141.9 | 29.6 | 70.4 | 42.9 | 190.55% | 60.94% |
| 9 | — | 33.2 | 66.8 | 39.3 | 177.45% | 58.83% |
| 10 | 145.2 | 36.4 | 63.6 | 36.1 | 165.82% | 56.76% |
| 11 | — | 39.6 | 60.4 | 32.9 | 154.18% | 54.47% |
| 12 | — | 43.2 | 56.8 | 29.3 | 141.09% | 51.58% |
| 13 | 146.6 | 45.8 | 54.2 | 26.7 | 131.64% | 49.26% |
| 14 | 147.3 | 47.8 | 52.2 | 24.7 | 124.36% | 47.32% |
| 15 | 140.0 | — | — | — | — | — |
| 16 | 125.2 | 52.4 | 47.6 | 20.1 | 107.64% | 42.23% |
| 17 | 144.8 | 53.6 | 46.4 | 18.9 | 103.27% | 40.73% |
| 18 | 143.2 | 56.2 | 43.8 | 16.3 | 93.82% | 37.21% |
| 19 | 143.9 | 57.0 | 43.0 | 15.5 | 90.91% | 36.05% |
| 20 | — | 58.4 | 41.6 | 14.1 | 85.82% | 33.89% |
| 21 | 153.5 | 60.0 | 40.0 | 12.5 | 80.00% | 31.25% |
| 22 | 146.8 | 61.5 | 38.5 | 11.0 | 74.55% | 28.57% |
| 23 | 148.8 | 62.7 | 37.3 | 9.8 | 70.18% | 26.27% |

TABLE 4.1-continued

| Time (m) | Temp (F.) | Loss in Weight Reading % | Weight Remaining % | Water Weight % of Total Mass | Moisture Content (Calculated) % Dry Basis | Moisture Content (Calculated) % Wet Basis |
|---|---|---|---|---|---|---|
| 24 | 155.3 | 63.8 | 36.2 | 8.7 | 66.18% | 24.03% |
| 25 | 152.2 | 64.9 | 35.1 | 7.6 | 62.18% | 21.65% |
| 26 | 149.3 | 66.0 | 34.0 | 6.5 | 58.18% | 19.12% |
| 27 | 156.3 | 66.8 | 33.2 | 5.7 | 55.27% | 17.17% |
| 28 | 151.7 | 68.1 | 31.9 | 4.4 | 50.55% | 13.79% |
| 29 | — | 68.1 | 31.9 | 4.4 | 50.55% | 13.79% |
| 30 | 145.4 | 68.6 | 31.4 | 3.9 | 48.73% | 12.42% |
| 31 | 151.0 | 69.0 | 31.0 | 3.5 | 47.27% | 11.29% |
| 32 | — | 69.4 | 30.6 | 3.1 | 45.82% | 10.13% |
| 33 | — | 69.8 | 30.2 | 2.7 | 44.36% | 8.94% |
| 34 | — | 70.2 | 29.8 | 2.3 | 42.91% | 7.72% |
| 35 | 143.2 | 70.8 | 29.2 | 1.7 | 40.73% | 5.82% |
| 36 | — | 71.4 | 28.6 | 1.1 | 38.55% | 3.85% |
| 37 | — | — | — | — | — | — |
| 38 | 154.9 | 71.4 | 28.6 | 1.1 | 38.55% | 3.85% |
| 39 | — | — | — | — | — | — |
| 40 | — | 72.1 | 27.9 | 0.4 | 36.00% | 1.43% |
| 41 | 146.0 | 72.0 | 28.0 | 0.5 | 36.36% | 1.79% |
| 50 | 146.0 | 72.5 | 27.5 | 0.0 | 34.55% | 0.00% |

In the second test, the rheostat was set to 90. An infrared thermometer was used to measure the temperature of the plant material being dried.

TABLE 4.2

| Time (m) | Temp (F.) | Loss in Weight Reading % | Weight Remaining % | Water Weight % of Total Mass | Moisture Content (Calculated) % Dry Basis | Moisture Content (Calculated) % Wet Basis |
|---|---|---|---|---|---|---|
| 0 | 82.4 | 0.0 | 100.0 | 72.5 | 298.18% | 72.50% |
| 1 | 142.8 | 4.6 | 95.4 | 67.9 | 281.45% | 71.17% |
| 2 | — | 7.5 | 92.5 | 65.0 | 270.91% | 70.27% |
| 3 | 147.3 | 12.0 | 88.0 | 60.5 | 254.55% | 68.75% |
| 4 | — | 19.8 | 80.2 | 52.7 | 226.18% | 65.71% |
| 5 | 149.1 | 26.8 | 73.2 | 45.7 | 200.73% | 62.43% |
| 6 | 162.3 | 34.8 | 65.2 | 37.7 | 171.64% | 57.82% |
| 7 | 182.3 | 41.8 | 58.2 | 30.7 | 146.18% | 52.75% |
| 8 | 172.9 | 47.0 | 53.0 | 25.5 | 127.27% | 48.11% |
| 9 | 212.0 | 51.6 | 48.4 | 20.9 | 110.55% | 43.18% |
| 10 | 187.8 | 55.7 | 44.3 | 16.8 | 95.64% | 37.92% |
| 11 | — | 59.2 | 40.8 | 13.3 | 82.91% | 32.60% |
| 12 | 211.1 | 62.6 | 37.4 | 9.9 | 70.55% | 26.47% |
| 13 | 211.0 | 64.5 | 35.5 | 8.0 | 63.64% | 22.54% |
| 14 | 217.7 | 67.0 | 33.0 | 5.5 | 54.55% | 16.67% |
| 15 | 216.8 | 68.4 | 31.6 | 4.1 | 49.45% | 12.97% |
| 16 | 226.0 | 69.0 | 31.0 | 3.5 | 47.27% | 11.29% |
| 16.5 | — | 70.0 | 30.0 | 2.5 | 43.64% | 8.33% |

In the third test, the rheostat was set to 120. An infrared thermometer was used to measure the temperature of the plant material being dried.

TABLE 4.3

| Time (m) | Temp (F.) | Loss in Weight Reading % | Weight Remaining % | Water Weight % of Total Mass | Moisture Content (Calculated) Dry Basis | Moisture Content (Calculated) Wet Basis |
|---|---|---|---|---|---|---|
| 0.0 | 83.4 | 0.0 | 100.0 | 72.5 | 298.18% | 72.50% |
| 1.0 | 139.6 | 3.2 | 96.8 | 69.3 | 286.55% | 71.59% |
| 2.0 | 146.6 | 11.0 | 89.0 | 61.5 | 258.18% | 69.10% |
| 3.0 | 141.2 | 20.6 | 79.4 | 51.9 | 223.27% | 65.37% |
| 4.0 | 144.5 | 28.5 | 71.5 | 44.0 | 194.55% | 61.54% |
| 5.0 | 148.4 | 35.0 | 65.0 | 37.5 | 170.91% | 57.69% |
| 6.0 | 154.9 | 42.2 | 57.8 | 30.3 | 144.73% | 52.42% |
| 7.0 | 165.5 | 48.4 | 51.6 | 24.1 | 122.18% | 46.71% |
| 8.0 | 174.0 | 52.2 | 47.8 | 20.3 | 108.36% | 42.47% |

TABLE 4.3-continued

| Time (m) | Temp (F.) | Loss in Weight Reading % | Weight Remaining % | Water Weight % of Total Mass | Moisture Content (Calculated) Dry Basis | Moisture Content (Calculated) Wet Basis |
|---|---|---|---|---|---|---|
| 9.0 | 176.0 | 56.6 | 43.4 | 15.9 | 92.36% | 36.64% |
| 10.0 | 180.1 | 60.2 | 39.8 | 12.3 | 79.27% | 30.90% |
| 11.0 | 193.6 | 63.2 | 36.8 | 9.3 | 68.36% | 25.27% |
| 12.0 | 196.1 | 66.6 | 33.4 | 5.9 | 56.00% | 17.66% |
| 13.0 | 181.2 | 68.2 | 31.8 | 4.3 | 50.18% | 13.52% |
| 14.0 | 217.4 | 69.6 | 30.4 | 2.9 | 45.09% | 9.54% |
| 15.0 | 202.6 | 70.8 | 29.2 | 1.7 | 40.73% | 5.82% |
| 15.5 | 157.4* | — | — | — | — | — |

* Temperatures dropped exceptionally fast when the cover was raised (i.e., about 20 F. in two to three seconds), and thus it was difficult to get accurate temperature readings depending on the location on the pile. After about 30 seconds, the temperature reading was 110 F.

As evidenced in the testing above, immature *Cannabis* plant leaves with very little stems may be dried under infrared heating to a moisture content of less than 15% in less than 30 minutes (rheostat 60) or less than 15 minutes (rheostat 90, 120).

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. A method of drying a *cannabis* plant material comprising an untrimmed, freshly harvested *cannabis* plant or at least one of an intact leaf, stalk, stem, flower, or bud of a freshly harvested *cannabis* plant, the method comprising:
   exposing the *cannabis* plant material to infrared radiation emitted from an infrared heater, the radiation having a wavelength of from about 3 to about 10 microns; and
   heating the *cannabis* plant material to a temperature of from about 100° F. to about 400° F.

2. The method of claim 1, wherein the *cannabis* plant material is exposed to the infrared radiation for a period of time such that less than 25% of a cannabinoid compound in the *cannabis* plant material is decarboxylated.

3. The method of claim 2, wherein the cannabinoid compound comprises cannabidiolic acid (CBDA).

4. The method of claim 2, wherein the cannabinoid compound comprises tetrahydrocannabinolic acid (THCA).

5. The method of claim 1, further including a step of circulating air over the *cannabis* plant material.

6. The method of claim 1, wherein the infrared heater is a catalytic gas heater operating at a gas pressure allowing heater output from 50% to 100% of rated power.

7. The method of claim 1, wherein the method does not comprise actively controlling the humidity of the air around the *cannabis* plant material while being exposed to the infrared radiation.

8. The method of claim 1, wherein the *cannabis* plant material does not exceed 180° F. during the heating step.

9. The method of claim 1, wherein the heating step comprises removing at least 10% of the moisture content from the *cannabis* plant material.

10. The method of claim 1, wherein the *cannabis* plant material is exposed to the infrared radiation for a period of time such that more than 75% of a cannabinoid compound in the *cannabis* plant material is decarboxylated.

11. The method of claim 10, wherein the *cannabis* plant material reaches a temperature of at least 285° F. during the heating step.

12. The method of claim 10, wherein the *cannabis* plant material is exposed to the infrared radiation for at least 3 minutes.

13. The method of claim 10, wherein the infrared heater is a catalytic gas heater operating at a gas pressure that allows heater output to vary from 50% to 100% of rated power.

14. The method of claim 1, wherein, prior to exposing the *cannabis* plant material to infrared radiation, the *cannabis* plant material is water cured for about 1 to about 10 hours.

15. The method of claim 1, wherein heating the *cannabis* plant material volatilizes water and terpenes from the *cannabis* plant material, the method further comprising condensing at least a portion of the water and terpenes.

16. The method of claim 15, further comprising extracting and recovering the terpenes from the water.

17. The method of claim 1, wherein the *cannabis* plant material is heated while in a cool or refrigerated environment having a temperature below about 70° F.

18. The method of claim 1, further comprising cooling the *cannabis* plant material to a temperature of from about 40° F. to about 90° F. and subsequently heating the *cannabis* plant material to a temperature of from about 100° F. to about 400° F.

19. The method of claim 1, wherein the method is capable of reducing the levels of *E. Coli, Salmonella*, Aflatoxin, and/or Ochratoxin below the detectable limits.

20. A method of decarboxylating a cannabinoid compound contained within a *cannabis* plant material comprising an untrimmed *cannabis* plant or at least one of an intact leaf, stalk, stem, flower, or bud of a *cannabis* plant, the method comprising:
   exposing the *cannabis* plant material to infrared radiation emitted from an infrared heater, the radiation having a wavelength of from about 3 to about 10 microns; and
   heating the *cannabis* plant material to a temperature of at least 200° F. for a sufficient time so as to decarboxylate at least 50% of the cannabinoid compound contained within the *cannabis* plant material.

21. The method of claim 20, wherein the cannabinoid compound comprises cannabidiolic acid (CBDA).

22. The method of claim 21, wherein at least 75% of the CBDA present within the *cannabis* plant material is decarboxylated into cannabidiol (CBD).

23. The method of claim 20, wherein the cannabinoid compound comprises tetrahydrocannabinolic acid (THCA).

24. The method of claim 23, wherein at least 75% of the THCA within the *cannabis* plant material is decarboxylated into tetrahydrocannabinol (THC).

25. A method of drying a *cannabis* plant material comprising an untrimmed, freshly harvested *cannabis* plant or at least one of an intact leaf, stalk, stem, flower, or bud of a freshly harvested *cannabis* plant while reducing the incidence of decarboxylation of a cannabinoid compound contained within the *cannabis* plant material, the method comprising:

exposing the *cannabis* plant material to infrared radiation emitted from an infrared heater, the radiation having a wavelength of from about 3 to about 10 microns; and
  heating the *cannabis* plant material to a temperature of from about 100° F. to about 160° F. to produce a dried *cannabis* plant material,
  wherein the dried *cannabis* plant material has a ratio of the cannabinoid compound to the decarboxylated cannabinoid compound of at least 2:1.

26. The method of claim 25, further including a step of circulating air over the *cannabis* plant material and not requiring a step of actively controlling the humidity of the air around the *cannabis* plant material.

27. The method of claim 25, wherein the *cannabis* plant material is exposed for a duration of time such that a moisture water content loss is at least 7.5%.

* * * * *